United States Patent [19]

Krivan et al.

[11] Patent Number: 5,217,715
[45] Date of Patent: Jun. 8, 1993

[54] CARBOHYDRATE RECEPTOR FOR BACTERIA AND METHOD FOR USE THEREOF

[75] Inventors: Howard C. Krivan, Rockville; Ginsburg Victor, Bethesda; David D. Roberts, Rockville, all of Md.

[73] Assignee: The United States of America as represented by the Department of Health and Human Services, Washington, D.C.

[21] Appl. No.: 226,445

[22] Filed: Aug. 1, 1988

[51] Int. Cl.$^5$ .................. G01N 33/53; A61K 31/70
[52] U.S. Cl. ..................... 424/92; 536/53; 536/123.1; 514/54; 435/253.3; 435/253.4; 435/851; 435/874; 435/882; 435/885
[58] Field of Search .................. 536/1.1, 53; 514/54; 435/253.3, 254.4, 851, 874, 882, 885; 424/92

[56] References Cited

U.S. PATENT DOCUMENTS 4,657,849  4/1987  Källenius et al. .................. 514/54
4,725,557  2/1988  Miyauchi et al. .................. 514/54

FOREIGN PATENT DOCUMENTS

86/04064  7/1986  World Int. Prop. O. ............ 514/54

*Primary Examiner*—Ronald W. Griffin
*Assistant Examiner*—Everett White
*Attorney, Agent, or Firm*—Lowe, Price, LeBlanc & Becker

[57] ABSTRACT

The invention is a carbohydrate receptor for pathogenic bacteria. The receptor is a purified carbohydrate compound that is a member selected from the group consisting of fucosyl-asialo GM1, asialo GM1, and asialo GM2. The invented receptor can be included in a composition having a pharmaceutically acceptable carrier. The invention includes methods for purifying, detecting, or removing bacteria from diseased tissue. The applicants have discovered a carbohydrate receptor for a variety of different species of disease-producing bacteria. The structure of the receptor is N-acetylgalactosamine-beta-1-4-galactose-beta-1-4-glucose, abreviated GalNAc$\beta$1-4Gal$\beta$1-4Glc. The receptor is present in human and animal tissues as complex molecules and can serve as the attachment site for bacterial infection. For example, fucosyl-asialo GM1, asialo GM1, and asialo GM2 are three biological molecules which occur in cell membranes and contain the carbohydrate receptor.

3 Claims, 6 Drawing Sheets

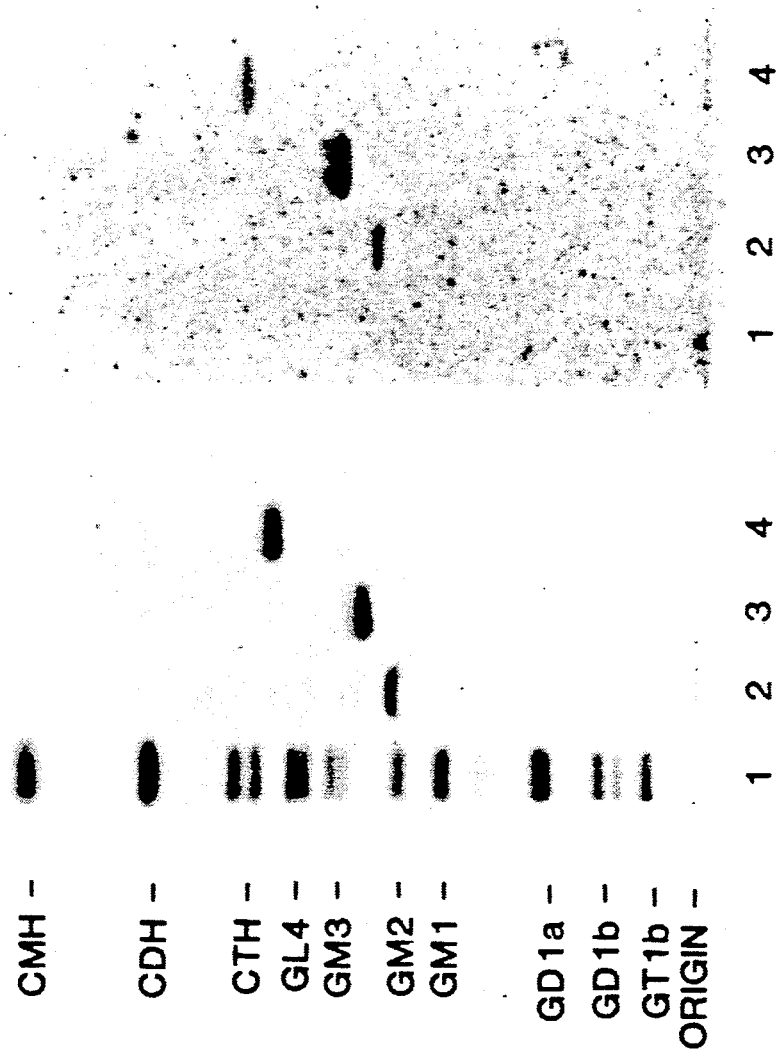

ial infection. For example, fucosyl-asialo GM1,
CARBOHYDRATE RECEPTOR FOR BACTERIA AND METHOD FOR USE THEREOF

BACKGROUND OF THE INVENTION

1. Field of the Invention

The invention relates generally to carbohydrate receptors and their use. Specifically, the invention relates to carbohydrate receptors for certain pathogenic bacteria their use in the detection, removal, or purification of such bacteria and their parts.

2. Description of the Background Art

Respiratory tract infections are a major health problem with as many as 1.5 million cases of pneumonia occurring in the United States each year with a high mortality rate. In addition, chronic lung infections, that are inevitable in patients suffering from cystic fibrosis, result in even higher rates of mortality, at 70 to 80 percent. The major groups of bacteria responsible for these infections are *Streptococcus pneumoniae, Staphylococcus aureus, Mycoplasma pneumoniae*, and several aerobic, gram-negative bacilli, including *Escherichia coli, Klebsiella pneumoniae*, and Pseudomonas and Haemophilus species. To cause pneumonia, an organism must invade the normally sterile lung parenchyma and establish a large enough population at its surface to cause disease. For this to occur, the infecting microbe is likely to attach to cell-surfaces. Although some type of adhesion has been described for these pathogens, the receptors that mediate their attachment have not been identified by direct binding.

Recently, glycosphingolipids have been reported to be cell surface receptors for some pathogenic bacteria analogous to their proposed role as receptors in other cell-cell and cell-ligand interactions. For example, uropathogenic *E. coli* specifically bind to Gal$\alpha$1-4Gal sequences in globoseries glycosphingolipids, that occur in the epithelial cells lining the urinary tract. Other bacteria that bind to glycosphingolipids include *Actinomyces naeslundii*, which binds to Gal$\beta$1-3GalNAc and GalNAc$\beta$1-3Gal sequences, and the *Propionibacterium granulosum* which binds to Gal$\beta$1-4Glc sequences.

The industry is lacking a carbohydrate receptor for many other pathogenic bacteria and a method for using the receptor in the purification, detection, and removal of those bacteria.

SUMMARY OF THE INVENTION

The applicants have discovered a carbohydrate receptor for a variety of different species of disease-producing bacteria. The structure of the receptor is N-acetylgalactosamine-beta-1-4-galactose-beta-1-4-glucose, abreviated GalNAc$\beta$1-4Gal$\beta$1-4Glc. The receptor is present in human and animal tissues as complex molecules and can serve as the attachment site for bacterial infection. For example, fucosyl-asialo GM1, asialo GM1, and asialo GM2 are three biological molecules which occur in cell membranes and contain the carbohydrate receptor.

Applicants do not purport to have discovered the receptor structure, since it is known to exist in many living cells from a variety of mammalian sources. Rather, the invention resides in the discovery that this structure is capable of specifically binding many different species of bacteria, including Pseudomonas, Haemophilus, Staphylococcus, and *Streptococcus pneumonia*. This binding specificity is novel to the art.

The receptor can be included in a composition having a pharmaceutically acceptable carrier, such that reagents containing the structure can be used for (i) removing pathogenic microorganisms from biological fluids or diseased tissue, (ii) detecting pathogenic microorganisms which may be present in biological fluids of tissue, (iii) purifying pathogenic bacteria or some part thereof, and (iv) inhibiting attachment of bacteria to diseased tissue in a preventive measure.

The invention is a carbohydrate receptor for many pathogenic bacteria. The "receptor" is a purified carbohydrate compound that is a glycolipid member selected from the group consisting of fucosyl-asialo GM1, asialo GM1, and asialo GM2. Any pure compound that contains the carbohydrate GalNAc$\beta$1-4Gcl is defined as a receptor for certain pathogenic bacteria.

The invented receptor can be included in a composition having a pharmaceutically acceptable carrier.

The invention includes a method for purifying these bacteria and parts thereof. The method provides the receptor or carbohydrate compound on an insoluble carrier. A media containing these selected bacteria with other species of bacteria is passed over the bound receptor compound. The selected bacteria adhere to the bound receptor compound and can be separated from the media and washed from the receptor compound.

The invention includes a method for detecting pathogenic bacteria. This method provides the receptor or carbohydrate compound on an insoluble carrier which can be suspended in a solution. When a culture of bacteria is added to the solution, these bacteria are detected by demonstrating a perceptible agglutination.

The invention includes a method for removing certain pathogenic bacteria from diseased tissue. This method provides the receptor compound in an aqueous pharmaceutical composition having a therapeutically effective concentration of the receptor or carbohydrate compound. The diseased tissue is then irrigated, flushed or, otherwise, washed with the aqueous pharmaceutical composition. The receptor compound binds with the bacteria and the action of the irrigated solution or aqueous pharmaceutical composition removes the bacteria from the diseased tissue.

BRIEF DESCRIPTION OF THE DRAWINGS

FIGS. 1A and 1B illustrate the binding of $^{125}$I-labeled bacteria to glycosphingolipids (which contain the receptor) separated by thin-layer chromatography.

DETAILED DESCRIPTION OF THE INVENTION

Figures 2B, 2C:
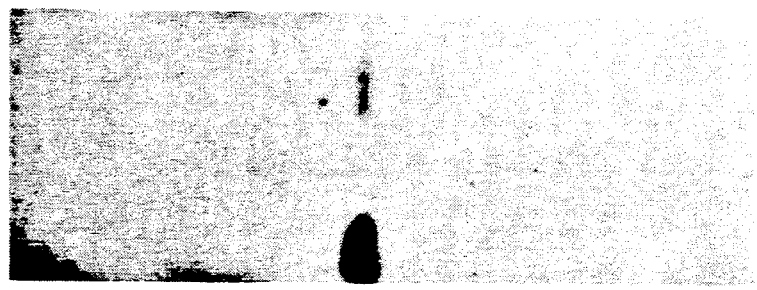
FIGS. 2A, 2B and 2C illustrate the detection of the "receptor", asialo GM1, in human lung extracts by immunostaining of thin-layer chromatograms.

Many pathogenic bacteria bind specifically to gangliotriosyl-ceramide (asialo GM2) and also, some other glycolipids that contain the carbohydrate sequence GalNAc$\beta$1-4Gal$\beta$1-4Glc. Part or all of this sequence may be the receptor on human tissues responsible for the adherence of these bacteria, which leads to colonization and infection. The GalNAc$\beta$1-4Gal$\beta$1-4Glc sequence incorporated into soluble carriers by conventional methods inhibit bacterial adherence. This property is important for treating burn patients and patients with cystic fibrosis who are infected with Staphylococcus or Pseudomonas. For example, treatment of infected tissue with a lavage containing asialo GM2 or the soluble carriers containing the sugar sequence can remove pathogenic bacteria; continued treatment can prevent recolonization and subsequent infection. The GalNAc$\beta$1-4Gal$\beta$1-4Glc sequence immobilized onto insoluble carriers by conventional methods can be used in agglutination tests to specifically detect bacteria, such as Staphylococcus in toxic shock syndrome or food poisoning.

The inventors have shown that *Pseudomonas aeruginosa* and *Pseudomonas cepacia* isolated from cystic fibrosis patients specifically bind to glycosphingolipids containing terminal or internal GalNAc1-4Gal sequences in an article Krivan, H., Ginsburg, V., Roberts, D., *Arch. Biochem. Biophys.* 260:493–496 (1988). The inventors have now discovered that other opportunistic pathogenic bacteria associated with respiratory tract infections also specifically bind to internal or terminal GalNAc$\beta$1-4Gal sequences occurring in glycosphingolipids such as fucosyl-asialo GM1, asialo GM1, and asialo GM2 (for structures see Table 1). The inventors can also demonstrate that asialo GM1 occurs in substantial amounts in human lung tissue.

Several pulmonary pathogenic bacteria were studied for binding to glycosphingolipids to examine the possible role of carbohydrates as adhesion receptors for infection. Radiolabeled bacteria were layered on thin-layer chromatograms or separated glycosphingolipids and bound bacteria were detected by autoradiography. The classic triad of infectious bacteria found in cystic fibrosis, *Pseudomonas aeruginosa, Haemophilus influenzae*, and *Staphylococcus aureus* along with other bacteria commonly implicated in typical pneumonia such as *Streptococcus pneumoniae, Klebsiella pneumoniae*, and certain *Escherichia coli* bind specifically to fucosyl-asialo GM1 (Fuc$\alpha$1-2Gal$\beta$1-3GalNAc$\beta$1-4Gal1-4Glc$\beta$1Cer), asialo GM1 (Gal$\beta$1-3GalNAc$\beta$1-4Gal$\beta$1-4Glc$\beta$1-1Cer), and asialo GM2 (GalNAc$\beta$1-4Gal$\beta$1-4Glc$\beta$1-1Cer). Bacteria maintained in nutrient medium bind better than the same cells suspended in buffer. They do not bind to galactosylceramide, glucosylceramide, lactosylceramide, trihexosylceramide, globoside, paragloboside, Forssman glycosphingolipid, or several other glycosphingolipids tested, including the gangliosides GM1, GM2, GM3, GD1a, GD1b, GT1b, and Cad. The finding that these pathogens do not bind to lactosylceramide suggest that $\beta$1-4-linked GalNAc. which is positioned internally in fucosyl-asialo GM1 and asialo GM1 and terminally in asialo GM2, is required for binding. $\beta$-GalNAc itself, however, is not sufficient for binding as the bacteria did not bind to globoside, which contains the terminal sequence GalNAc$\beta$1-3Gal. These data suggest that these bacteria require at least terminal or internal GalNAc$\beta$1-4Gal sequences unsubstituted with sialyl residues for binding. Other bacteria such as *Mycoplasma pneumoniae, Streptococcus pyogenes*, Salmonella sp., and some *E. coli* do not bind to the GalNAc$\beta$1-4Gal sequence. The biological relevance of these data is suggested by our finding that substantial amounts of asialo GM1 occur in human lung tissue.

The following examples demonstrate the invention.

EXAMPLE 1

The following materials and methods were used in Example 1.

Mouse monoclonal anti-asialo (IgM, k) and mouse monoclonal anti-asialo GM2 (2D4, IgM, ATCC TIB185) were obtained from Baylor College of Medicine and the National Institutes of Health, respectively. Affinity purified goat anti-mouse IgM obtained from Kirkegaard and Perry Laboratories, Gaithersburg, Md., and protein A (Pharmacia, Inc. Piscataway, N.J.) were labeled with $^{125}$I (ICN Biomedicals, Costa Mesa, Calif.) by the known "Iodogen method" to a specific activity of approximately 50 $\mu$Ci/ug. Bovine tests $\beta$-galactosidase and bovine serum albumin (BSA fraction V) was purchased from Boehringer-Mannheim Biochemicals, Indianapolis, Ind. DL-Dihydrolactocerebroside (CDH) was obtained from Calbiochem, San Diego, Calif. Ganglioside GM3 was purified from normal human kidney as is known in the art. Paragloboside derived from type O human and sheep erythrocytes respectively. Ganglioside and neutral glycosphingolipid standards were purchased from Supelco, Bellefonte, Pa. and Sigma Chemical Company, St. Louis Mo. Cad ganglioside from human erythrocytes were from Baylor College of Medicine. Fildes enrichment and brain heart infusion (BHI), Trypticase soy, and Penassay (antibiotic medium 3) dehydrated media were purchased from Difco Laboratories, Detroit, Mich. GC-enriched chocolate agar plates were purchased from Remel, Lenexa, Kansas. Blood agar. BHI agar, Luria-Bertani broth(LB-broth) and Trypticase soy agar slants were obtained from the NIH Media Services, Bethesda, Md. Polyisobutylmethacrylate was purchased from Polysciences, Warrington, Pa.

The bacteria used and their sources are described in Table 2. Bacteria were stored at $-70°$ C. until used and maintained on Trypticase soy agar slants or blood and chocolate agar plates depending on the species. *M. pneumoniae* metabolically labeled with [$^3$H]palmitic acid was kindly provided by Mycoplasma Branch, Division of Bacterial Products, FDA. The other bacteria were routinely grown in Trypticase soy broth without added glucose, LB-Broth, or Penassay broth for 18 h in 100 ml of medium in 125 ml screw cap bottles at 37° C. without shaking. For growth of *H. influenzae*, Trypticase soy broth was supplemented with Fildes enrichment. Broth cultures were centrifuged at 4° C. and 8,000 g for 20 minutes and pellets were washed three times in 0.01M sodium phosphate, pH 7.2, containing 0.15M sodium chloride (PBS). Radioiodination of bacteria was performed by known techniques. The labeled bacteria were suspended to $10^7$–$10^8$ cells/ml in either LB-broth or 0.05M Tris-HCl pH 7.4 containing 0.15M sodium chloride and 1 percent bovine serum albumin (TBS-BSA). Metabolic labeling of bacteria was achieved by adding [6-$^3$H]glucose to 100 ml of Trypticase soy broth without added glucose (5 $\mu$Cl/ml, 11 Ci/mmol; ICN) before inoculation with 0.1 ml of suspension of bacteria (approximately $10^7$ cells/ml) obtained from an overnight culture of the same medium. Cells were incubated 18 hours at 37° C. without shaking, collected and washed by centrifugation as above and suspended to $10^7$–$10^8$ cells/ml ($5 \times 10^5$ to $1 \times 10^6$ cpm/ml) in LB-broth or TBS-BSA.

Bacteria bound to separated glycosphingolipids were detected by known techniques. Briefly, glycosphingolipids were chromatographed on aluminum-backed silica gel 60 high performance plates (Merck, West Germany) in chloroform: methanol:0.25% aqueous KCI (5:4:1). After drying, the plates were coated with 0.1% polyisobutylmethacrylate and air dried. The plates were sprayed with TBS-BSA and immersed in this buffer for 1 hour. The plates were then overlaid for 3 hours at 4° C. or room temperature with 60 μl/cm² of radioiodinated bacteria (approximately $1 \times 10^6$ to $5 \times 10^6$ cpm/ml; $10^7$–$10^8$ cells/ml), washed gently by dipping in five successive changes of PBS at one-minute intervals, dried and exposed to XAR-5 X-ray film (Eastman Kodak, Rochester, N.Y.) for approximately 12 hours.

The binding of bacteria to purified glycosphingolipids immobilized in flat-bottom wells of polyvinylchloride microtiter plates (Falcon 3912-III, Becton-Dickinson) was done as according to known techniques. Briefly, glycosphingolipids were serially diluted in 25 μl of methanol containing 0.1 μg (4 μg/ml) each of the auxillary lipids dipalmitoyl phosphatidyloholine (Sigma) and cholesterol (Sigma grade I), and dried by evaporation. The wells were filled with TBS-BSA and incubated 2 hours at room temperature to block nonspecific binding sites, emptied, and $1 \times 10^5$ to $1 \times 10^6$ cpm of labeled bacteria in 25 μl of LB-broth or TBS-BSA were added. The plate was covered with parafilm and incubated at room temperature for 2 hours. The wells were washed five times with PBS using a pasteur pipet, cut from the plate and bound radiolabeled bacteria was quantified.

Normal human lung tissue was obtained at autopsy through the cooperation of the Department of Pathology, Fairfax Hospital, Falls Church, Va. and the Department of Pediatrics, University of Texas Medical Branch, Galveston, Tex. Tissue was immediately frozen at −70° C. until used. Lung tissue (120 g) was homogenized in a blender with water and extracted twice with chloroform: methanol:water (4:8:3). The total lipid extract was dried, subjected to mild alkaline degradation, neutralized, dialyzed, extensively against distilled water (above its critical micellar concentration), and lyophilized. The neutral and acidic glycosphingolipids were separated by chromatography on DEAE-Sepharose. Alkali-stable lipid contaminants were eliminated from the neutral glycosphingolipid fraction by acetylation, followed by Florsil column chromatography, and deacetylation.

Glycosphingolipid antigens were detected on thin layer chromatograms by immunostaining according to known techniques. Briefly, human neutral lung glycosphingolipids and standards were separated by thin-layer chromatography and plates were coated with polyisobutylmethacrylate and blocked with TBS-BSA as described for the bacteria overlay assay. The chromatograms were then overlaid with 60 μl/cm² of TBS-BSA containing either mouse monoclonal anti-asialo GM1 (lug/ml) or mouse monoclonal anti-asialo GM2 (5 μg/ml), and incubated overnight at 4° C. Chromatograms were washed five times in PBS and overlaid with $3 \times 10^6$ cpm/ml of $^{125}$I-labeled affinity purified goat anti-mouse IgM. After incubation for 1 hour at room temperature, the plates were washed with the PBS, dried, and exposed for approximately 12 hours to X-ray film.

Fucosyl-asialo GM1 and asialo GM1 were prepared from bovine brain gangliosides by hydrolysis in 0.05 NH$_2$SO$_4$ for 1.5 hours at 80° C. The hydrolysate was neutralized with NH$_4$OH, dried under nitrogen, the residue was disolved in chloroform: methanol:water (60:30:4.5), and non-glycosphingolipid contaminants were removed Sephadex G-25 column chromatography. Fucosyl-asialo GM1 and asialo GM1 were separated from residual gangliosides by column chromatography on DEAE Sepharose and further purified by continuous thin-layer chromatography on preparative silica gel G plates using chloroform:methanol: water (75:18:2.5). Asialo GM2 was obtained after digestion of asialo GM1 with bovine testes β-galactosidase (0.5 units/ml) for 36 hours at 37° C. in 0.1M acetate buffer, pH 5.0, containing 0.2 percent sodium taurocholate. Polar contaminants and detergent were removed by G-25 and DEAE-Sepharose column chromatography, respectively.

The following results were obtained in Example 1.

Previous data has shown that P. aeruginosa and P. cepacia isolated from patients with cystic fibrosis bind specifically to asialo GM1 and asialo GM2 by recognizing at least the GalNAcβ1-4Gal sequence in these glycosphingolipids. Because these bacteria are notorious lung pathogens generally restricted to this patient population, other bacteria that cause respiratory tract infections were tested for binding to the same glycosphingolipids. Glycosphingolipid standards were subjected to thin-layer chromatography and analyzed for their ability to bind the bacteria listed in Table 2. As shown by the autoradiogram of FIG. 1B, compared to a similar thin-layer chromatogram of glycosphingolipids detected by orcinol reagent (FIG. 1A), H. influenza bound specifically to fucosyl-asialo GM1, asialo GM1 and asialo GM2, but not to other glycosphingolipids in Table 1 tested at 1–5 μg. Similar results were obtained with the other bacteria listed as positive for binding in Table 2. Interestingly, the lung pathogen M. pneumoniae did not bind, nor did the group A streptococci or several enteric bacteria. Tables 1 and 2 are as follows.

TABLE 1

| Glycolipid | Structures of glycolipids tested for binding bacteria Structure* |
|---|---|
| Fucosyl-asialo GM1 | Fucα1-2Galβ1-3GalNAcβ1-4Galβ1-4Glcβ1-1Cer |
| Asialo GM1 | Galβ1-3GalNAcβ1-4Galβ1-4Glcβ1-1Cer |
| Asialo GM2 | GalNAcβ1-4Galβ1-4Glcβ1-1Cer |
| Asialo Cad | GalNAcβ1-4Galβ1-4GlcNAcβ1-3Galβ1-4Glcβ1-1Cer |
| Sulfatide | SO$_3$−−Galβ1-1Cer |
| Galactosyl ceramide (CMH) | Galβ1-1Cer |
| Glucosyl ceramide (CMH) | Glcβ1-1Cer |
| Lactosyl ceramide (CDH) | Galβ1-4Glcβ1-1Cer |
| Trihexosyl ceramide (CTH) | Galα1-4Galβ1-4Glcβ1-1Cer |
| Paragloboside | Galβ1-4GlcNAcβ1-3Galβ1-4Glcβ1-1Cer |
| Globoside (GL4) | GalNAcβ1-3Galα1-4Galβ1-4Glcβ1-1Cer |
| Forssman | GalNAcα1-3GalNAcβ1-3Galα1-4Galβ1-4Glcβ1-1Cer |

TABLE 1-continued

Structures of glycolipids tested for binding bacteria

| Glycolipid | Structure* |
|---|---|
| GM3 | NeuAcα2-3Galβ1-4Glcβ1-1Cer |
| GM2 | GalNAcβ1-4[NeuAcα2-3]Galβ1-4Glcβ1-1Cer |
| GM1 | Galβ1-3GalNAcβ1-4[NeuAcα2-3]Galβ1-4Glcβ1-1Cer |
| GD1a | NeuAcα2-3Galβ1-3GalNAcβ1-4[NeuAcα2-3]Galβ1-4Glcβ1-1Cer |
| GD1b | Galβ1-3GalNACβ1-4[NeuAcα2-8NeuAcα2-3]Galβ1-4Glcβ1-1Cer |
| GT1b | NeuAcα2-3Galβ1-3GalNAcβ1-4[NeuAcα2-8NeuAcα2-3]Galβ1-4Glcβ1-1Cer |
| Cad | GalNACβ1-4[NeuAcα2-3]Galβ1-4GlcNAcβ1-3Galβ1-4Glcβ1-1Cer |

*The underline indicates the probable minimum sequence required for binding

TABLE 2

Bacteria tested for binding to GalNAcβ1-4Gal sequences found in fucosyl-asialo GM1, asialo GM1, and asialo GM2.

| Microorganism | Source* | Binding+ | Comment |
|---|---|---|---|
| *Streptococcus pneumoniae* 33400 | ATCC | + | Type Strain |
| *Streptococcus pneumoniae* 6303 | ATCC | + | Type III Capsule |
| *Streptococcus pneumoniae* 27336 | ATCC | + | Rough Phase |
| *Staphylococcus aureus* 12600 | ATCC | + | Neotype Strain |
| *Staphylococcus aureus* 8095 | ATCC | + | |
| *Haemophilus influenzae* 33391 | ATCC | + | Type Strain |
| *Haemophilus influenzae* 9795 | ATCC | + | Type B Capsule |
| *Haemophilus parainfluenzae* 33392 | ATCC | + | Type Strain |
| *Klebsiella pneumoniae* 27736 | ATCC | + | |
| *Pseudomonas aeruginosa* CT3 | Human | + | CF patient, Mucoid |
| *Pseudomonas aeruginosa* CT4 | Human | + | CF patient, Mucoid |
| *Pseudomonas aeruginosa* CT5 | Human | + | CF patient, Mucoid |
| *Pseudomonas aeruginosa* 17648 | ATCC | + | |
| *Pseudomonas aeruginosa* 19142 | ATCC | + | Mucoid |
| *Pseudomonas aeruginosa* 33347 | ATCC | + | Rough Phase |
| *Pseudomonas aeruginosa* 21472 | ATCC | + | |
| *Pseudomonas cepacia* 25416 | ATCC | + | Type Strain |
| *Pseudomonas cepacia* ML1 | Human | + | CF patient |
| *Pseudomonas cepacia* 13945 | ATCC | + | |
| *Pseudomonas maltophilia* 13637 | ATCC | + | Type Strain |
| *Escherichia coli* VJ1 | NIH | + | |
| *Escherichia coli* 6883 | ATCC | + | |
| *Mycoplasma pneumoniae* M129 | FDA | − | |
| *Streptococcus pyogenes* 12344 | ATCC | − | Type Strain |
| *Salmonella milwaukee* U4 4407-50 | CDC | − | |
| *Salmonella enteritidis* 13076 | ATCC | − | Type Strain |
| *Escherichia coli* K1 | NIH | − | |
| *Escherichia coli* K99 1472 (B44) | URI | − | 09:K30, K99, F41:NM |

*ATCC, American Type Culture Collection; CDC, Center for Disease Control; NIH, National Institutes of Health; FDA, Food and Drug Administration; URI, University of Rhode Island.
+Bacteria were tested for binding to glycosphingolipids by using the bacteria overlay assay as described in Materials and Methods. A (+) indicates binding and a (−) indicates no binding to at least 2 ug of glycosphingolipid containing the GalNAcβ1-4Gal sequence.

The pulmonary pathogens bind to asialo-gangliosides after they are cultured in either Trypticase soy broth, LB-broth or Penassay broth under static conditions at 37° C. for 18 hours. *P. aeruginosa* does not bind well when grown on agar (other bacteria were not tested). Thus, binding of this organism may depend on culture conditions as has been described for other bacterial adhesions. To exclude the possibility that a high molecular weight component of the growth medium was mediating binding of bacteria to there glycospingolipids, *P. aeruginosa* CT4 was grown in Trypticase soy broth which had been filtered through a membrane with a molecular weight cut off of 3,000. This treatment did not affect the binding of *P. aeruginosa* to asialo GM1.

After bacteria were radiolabeled and washed as described in Material and Methods, the cells were suspended in either LB-broth or in isotonic buffer (TBS-BSA). Cells maintained in a nutrient medium bound better than cells suspended in TBS-BSA and remained viable for a longer time (data not shown). Therefore, LB-broth was used as diluent for bacteria in all experiments in this investigation. Non-viable bacteria did not bind to glycosphingolipids in the assays. Some bacteria, particularly the pneumococci, when maintained in non-nutrient media quickly lost their ability to bind to asialo gangliosides. These results are consistent with recent reports that bacterial attachment to carbohydrate receptors requires favorable growth conditions so that at least minimal protein synthesis can occur, and that bacteria that bind to glycospingolipid receptors on thin-layer chromatograms are viable while attached.

The pulmonary pathogens do not bind to 5 μg of actosylceramide. Thus, β-N-acetylgalactosamine, which is positioned internally in fucosyl-asialo GM1 and asialo GM1 and terminally in asialo GM2, is required for binding. N-Acetylgalactosamine alone, however, is not sufficient because the bacteria do not bind to globoside, which contains a terminal GalNAcβ1-3Gal sequence, or to the Forssman glycosphingolipid, which contains a terminal GA1NAcα1-3GalNAc sequence (Table 1). In addition, these pulmonary pathogens do not bind to the gangliosides GM1, GM2, GD1a, GD1b, GT1b, and Cad which all contain the GalNacβ1-4Gas sequence, suggesting that the sialyl residues prevent binding.

The biological relevance of these data is suggested by the presence of asialo GM1 in human lung extracts.

Neutral glycosphingolipids from human lung were separated by thin layer chromatography and immunostained using monoclonal antibodies specific for asialo GM1 and asialo GM2. As shown in FIG. 2B, anti-asialo GM1 antibody bound only to authentic asialo GM1 and to an antigen with the same mobility in the neutral lung fraction, indicating the presence of asialo GM1 in this fraction. The antigen was also verified to be asialo GM1 by comigration with the authentic glycosphingolipid in two other solvent systems as detected by orcinol and immunostaining (data not shown). Asialo GM2 was not detected by immunostaining in the neutral lung fraction (FIG. 2C).

Figure 3:
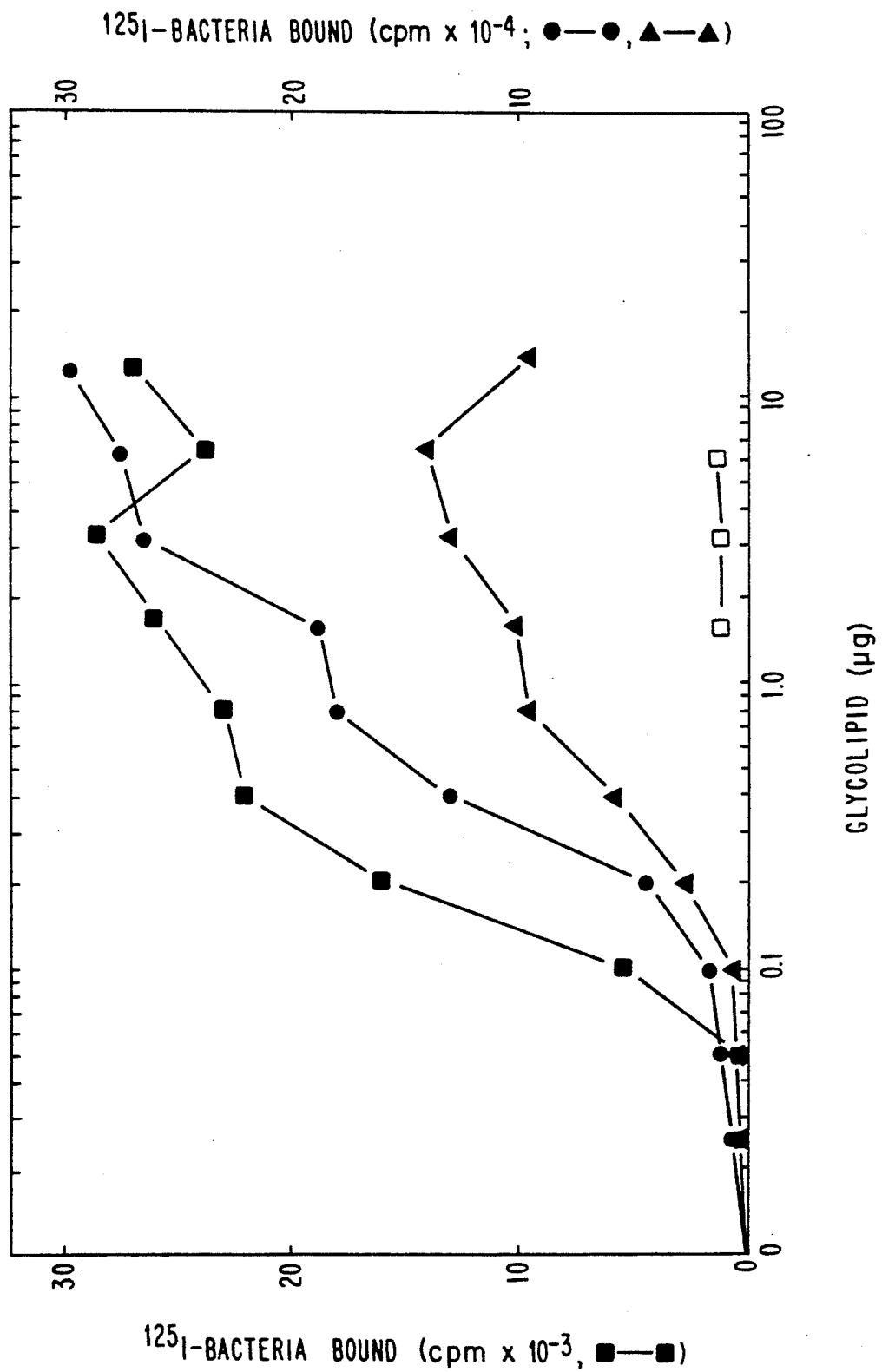
FIG. 3 illustrates the solid phase binding assay for some pathogenic bacteria.
Figure 4:
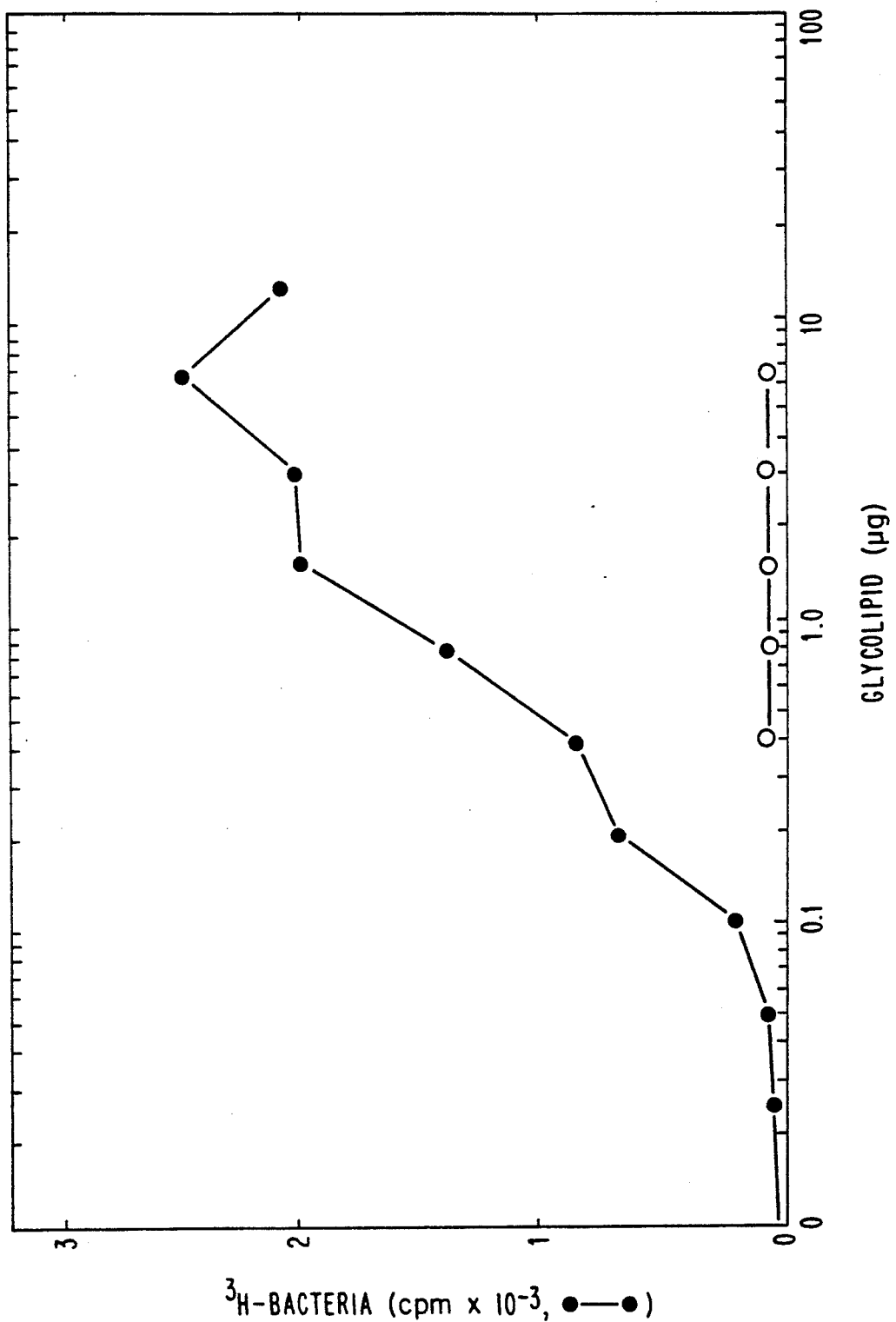
FIG. 4 illustrates the solid phase binding assay for metabolically labeled *H. influenza.*

The binding avidity of a representative group of bacteria from Table 2 for asialo GM1 was estimated by dilution curves from microtiter wells (FIG. 3). All three pathogens tested exhibit similar binding curves in the solid phase binding assay for asialo GM1 and compared with the previously reported data for $P.$ $aeruginosa$ and $P.$ $cepacia$ cited above. Glycosphingolipids immobilized onto microtiter wells which did not contain the GalNAc$\beta$1-4Gal sequence were not receptors for the bacteria. Binding of $^3$H-labeled $H.$ $influenza$ demonstrates that the specificity for asialo GM1 is not an artifact of radioiodination (FIG. 4).

The data presented in this paper show that $S.$ $pneumoniae$, $S.$ $aureus$, $H.$ $influenzae$. $K.$ $pneumoniae$, certain $E.$ $coli$, and several species of Pseudomonas specifically recognize the carbohydrate sequence GalNAc$\beta$1-4Gal found in fucosyl-asialo GM1, asialo GM1 and asialo GM2. The ability of these bacteria to recognize internal or terminal sequences clearly enhances their adhesion potential as lung pathogens, since cells could contain several different glycosphingolipids with this sequence. This is true in the case of certain $E.$ $coli$ that cause urinary tract infections, which recognize terminal and internal Gal$\alpha$1-4Gal sequences in glycosphingolipids. Asialo GM1, but not asialo GM2, was detected in glycosphingolipids from human lung tissue, but other glycosphingolipids or glycoproteins containing the GalNAc$\beta$1-4Gal sequence may also bind the bacteria. For example, glycoproteins with blood group Sd$^a$ and Cad specificity which contain this sequence occur in many human secretions. Glycosphingolipids with the blood group Cad determinant (Table 1) when desialylated bind $P.$ $aeruginosa$ (data not shown).

Some viruses, including influenza, express a neuraminidase and change the morphology of the lung by destroying ciliated epithelium. Neuraminidase decreases the viscosity of the lung mucus which may predispose individuals to secondary pneumonia by many of the pathogens listed in Table 2. The purified enzyme in vitro increases the adhesion of oral bacteria to human buccal epithelial cells. The respiratory tract of animals infected with influenza virus exhibit enhanced adhesion of several bacteria including $P.$ $aeruginosa$, $H$ $influenzae$, $S.$ $aureus$, and $S.$ $pneumoniae$. In addition, mice are susceptible to bacterial pneumonia only after persistent infection with influenza A virus. A possible explanation as to why influenza virus and pathogenic bacteria might interact in the pathogenesis or pneumonia could be that the viral neuraminidase may desialylate carbohydrate sequences on the cells lining the respiratory tract and increase the number of structures containing unsubstituted GalNAc$\beta$1-4Gal residues. Interestingly, $P.$ $aeruginosa$ adhere to mouse tracheas treated with 0.1 N HCl, again possibly due to hydrolysis of acid-labile sialyl residues.

In summary, several pathogenic bacteria, both gram positive and gram negative, bind specifically to GalNAc$\beta$1-4Gal sequences found in fucosyl-asialo GM1, asialo GM1, and asialo GM2. Although these microorganisms belong to different genera, when infectious they all have in common a high degree of tissues tropism for the respiratory tract. The possible use by these organisms of the same cell surface receptors for colonization might explain this common tropism. Consistent with this observation is the finding that asialo GM1 occurs in substantial amounts in human lung tissue.

The results of Example 1 are understood by reference to FIGS. 1 through 4.

FIG. 1 illustrates the binding of $^{125}$I-labeled bacteria to glycosphingolipids separated by thin-layer chromatography. The chromatography and thin-layer overlay procedure were carried out as described above. "A" is standard glycosphingolipids detected with orcinol reagent and "B" is Glycosphingolipids detected by autoradiography with radioiodinated $H.$ $influenzae$ ATCC 9795. Lane 1 is 2 $\mu$g galactosyl ceramide (CMH), 2 $\mu$g lactosylceramide (CDH), 2 $\mu$g trihexosyl ceramide (CTH), 2 $\mu$g globoside (GL4), and the gangliosides GM3 (2 $\mu$g), GM2 (2 $\mu$g), GM1 (2 $\mu$g), GD1a (2 $\mu$g), GD1b (2 $\mu$g), and GT1b (2 $\mu$g). Lane 2 is 1 $\mu$g fucosyl gangliotetraosylceramide (fucosyl-asialo GM1). Lane 3 is 1 $\mu$g gangliotetraosylceramide (asialo GM1). Lane 4 is 1 $\mu$g gangliotriaosylceramide (asialo GM2). For structures, see Table 1.

Figure 2A:
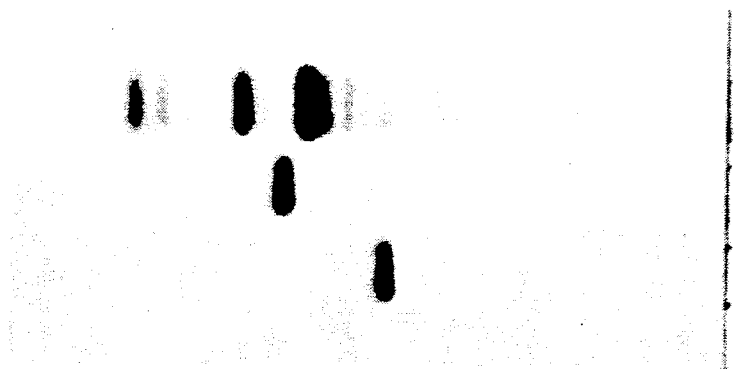

FIG. 2 illustrates the detection of asialo GM1 in human lung extracts by immunostaining of thin-layer chromatograms as described above. "A" is glycosphingolipids detected by orcinol spray. "B" is immunostaining with mouse anti-asialo GM1 monoclonal antibody (1 $\mu$g/ml). "C" is immunostaining with mouse anti-asialo GM2 monoclonal antibody (5 $\mu$g/ml). Lane 1 is 25 ng gangliotetraosylceramide (asialo GM1). Lane 2 is 50 ng gangliotriosylceramide (asialo Gm2). Lane 3 is total human lung neutral glycosphingolipid fraction from 100 mg wet weight of tissue.

FIG. 3 is the solid phase binding assay for some pathogenic bacteria. The assay was carried out as described above using approximately 10$^7$ cells/well with glycosphingolipids serially diluted in microtiter wells. The following symbols are used for binding of $^{125}$I-labeled $S.$ $pneumoniae$ (■), $S.$ $aureus$ (●), $H.$ $parainfluenzae$ (▲) to asialo GM1. Binding of $S.$ $pneumoniae$ to CMH, CDH, CTH, GL4 or GM1 (□).

FIG. 4 is the solid phase binding assay for metabolically labeled $H.$ $influenzae$. The assay was carried out as described above using approximately 10$^7$ cells/well with glycosphingolipids serially diluted in microtiter wells. The following symbols are used for binding of [$^3$H]-labeled $H.$ $influenzae$ to asialo GM1 (●) and to CMH CDH, CTH GL4 or GM1 (O).

EXAMPLE 2

$Pseudomonas$ $aeruginosa$ infection in the lungs is a leading cause of death of patients with cystic fibrosis, yet a specific receptor that mediates adhesion of the bacteria to host tissue has not been identified. To examine the possible role of carbohydrates for bacterial adhesion, two species of Pseudomonas isolated from patients with cystic fibrosis were studied for binding to glycolipids. $P.$ $aeruginosa$ and $P.$ $cepacia$ labeled with $^{125}$I were layered on thin-layer chromatograms of separated glycolipids and bound bacteria were detected by autoradiography. Both isolates bound specifically to asialo GM1

(Gal$\beta$1-3GalNAc$\beta$1-4Gal$\beta$1-4Glc$\beta$1-1Cer and asialo GM2 (GalNAc$\beta$1-4Gal$\beta$1-4Glc$\beta$1-1Cer) but not to lactosylceramide (Gal$\beta$1-4Glc$\beta$1-1Cer), globoside (GalNAc$\beta$1-3Gal$\alpha$1-4Gal$\beta$1-4Glc$\beta$1-1Cer), paragloboside (Gal$\beta$1-4GlcNAc$\beta$1-3Gal$\beta$1-4Glc$\beta$1-1Cer) or several other glycolipids that were tested. Asialo GM1 and asialo GM2 bound the bacteria equally well, exhibiting similar binding curves in solid-phase binding assays with a detection limit of 200 ng of either glycolipid. Both isolates also did not bind to GM1, GM2 or GD1a suggesting that substitution of the glycolipids with sialosyl residues prevents binding. As the Pseudomonas do not bind to lactosylceramide, the $\beta$-N-acetylgalactosamine residue, positioned internally in asialo GM1 and terminally in asialo GM2, is probably required for binding. $\beta$-N-acetylgalaotosamine itself, however, is not sufficient as the bacteria do not bind to globoside or to Forssman glycolipid. These data suggest that P. aeruginosa and P. cepacia recognize at least terminal or internal GalNAc$\beta$1-4Gal sequences in glycolipids which may be receptors for these pathogenic bacteria.

Cystic fibrosis (CF)[2] strikes an estimated 1 in every 2000 babies born in the United States, and affected children have only a 50 percent chance of surviving to the age of 21. A major cause of death of patients with CF is respiratory failure due to an overwhelming infection with Pseudomonas aeruginosa. Once established, this serious toxigenic pathogen is never completely eradicated from the lung, but persists in number up to $10^8$ organisms per ml sputum. The success of P. aeruginosa to preferentially colonize the lungs of CF patients suggest that specific receptors mediate adherence of the organism, which is an important first step in the pathogenesis of infectious disease. To examine the role of possible carbohydrates as adhesion receptors, two species of Pseudomonas isolated from CF patients were studied for binding to glycolipids. This example demonstrates that P. aeruginosa and P. cepacia bind specifically to asialo GM1 and asialo GM2, both of which contain the carbohydrate sequence GalNAc$\beta$1-4Gal.

P. aeruginosa CT3, CT4 and CT5 were nonmucoid clinical isolates from sputum samples from CF patients and were kindly provided by NIDDK, Bethesda, Md. P. aeruginosa (ATCC 17648 and 19142) were mucoid strains purchased from the American Type Culture Collection, Rockville, Md. P. cepacia ML2 was obtained from a CF patient upon bronchioscopy and was kindly supplied by the University of Texas Medical Branch, Galveston, Tex. Bacteria were maintained on trypticase soy slants at room temperature and were cultured in trypticase soy broth for 18 hours at 37° C. without shaking. Broth cultures were centrifuged at 4° C. and 10,000$\times$g for 20 minutes and pellets were washed 3 times in 0.01M sodium phosphate, pH 7.2, containing 0.15M sodium chloride (PBS). Radioiodination of bacteria was performed using a known procedure of Karlsson with modification as phosphate buffer pH 6.8) were transfected to a 10$\times$75 mm test tube previously coated with 100 $\mu$g of Iodogen, and reacted with 1 mCi of Na $^{125}$I at 4° C. for 10 minutes followed by a 5 minute incubation at room temperature. The iodination was terminated by removing the cells from the reaction tube, followed by centrifugation and 3 washes in 0.05M Tris-HCI, pH 7.8, containing 0.15M sodium chloride and 1 percent bovine serum albumin (TBS-BSA). The labeled bacteria were resuspended to $5\times10^7$–$10^8$ cells per ml in TBS-BSA.

For the detection of glycolipid receptors using labeled bacteria as a probe, we used a thin-layer overlay procedure first described for cholera toxin and modified later for bacteria. Briefly, thin-layer chromatography of glycolipids was carried out on aluminum-backed silica gel high performance plates (E. Merck, West Germany) developed with chloroform:methanol:0.25 percent acqueous KCl (50:40:10). After chromatography the plates were dried, dipped in hexane containing 0.1 percent polyisobutlmethacrylate and air dried. The plates were sprayed with TBS-BSA and then immersed in this buffer for 1 hour. After excess buffer was drained from the plates, they were overlaid for 4 hours with 60 $\mu$l/cm$^2$ of $^{125}$I-labeled bacteria (approximately $10^6$ cpm/ml; $5\times10^7$–$10^8$ cells/ml) in TBS-BSA. The plates were washed 5 times with PBS to remove unbound bacteria, dried and exposed overnight to XAR-5 X-ray film (Eastman Kodak, Rochester, N.Y.) at room temperature.

Figures 5A, 5B:
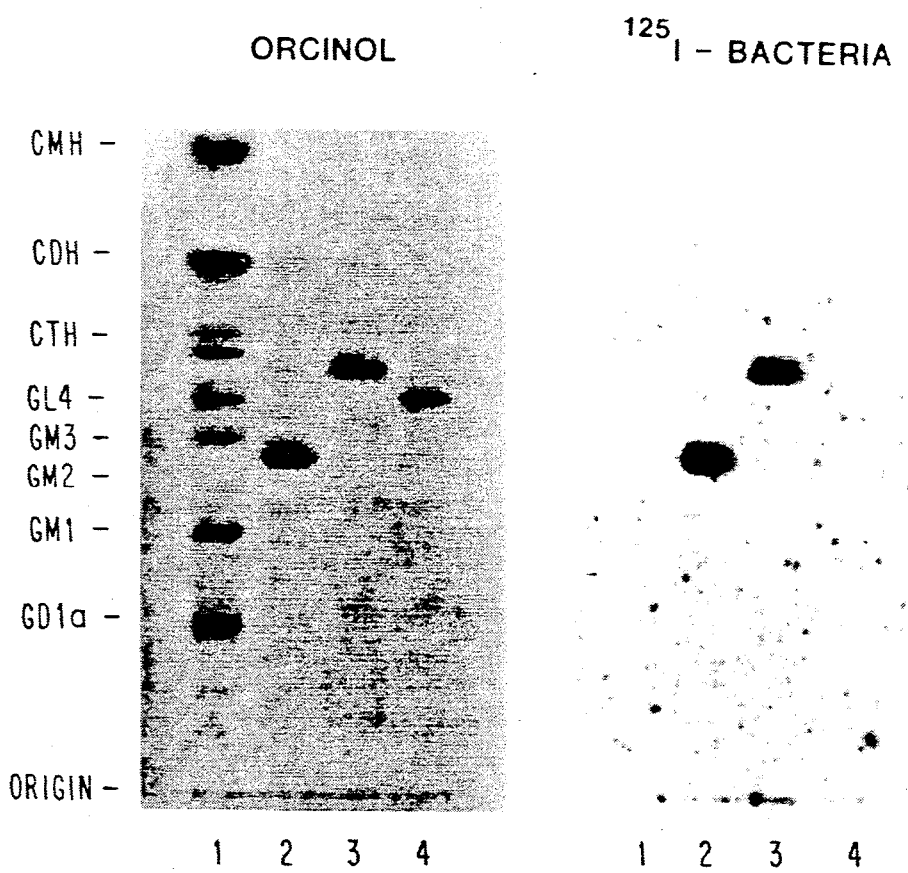
FIGS. 5A and 5B illustrate the direct binding of $^{125}$I-labeled *P. aerugmosa* CT3 to receptor glycolipids separated by thin-layer chromatography.

Mixed and purified glycolipid standards were subjected to thin layer chromatography and analyzed for their ability to bind bacteria by this overlay procedure. As shown by the autoradiogram (FIG. 5B), compared to an identical thin-layer chromatographic pattern of glycolipids detected by orcinol spray (FIG. 5A), P. aeruginosa CT3 bound specifically to asialo GM1 and the product obtained after $\beta$-galactosidase digestion, asialo GM2, but not to other glycolipids tested at 1-5 $\mu$g as shown in Table 3.

TABLE 3

| Glycolipid | Structure[a] |
|---|---|
| | Structures of Glycolipids Tested for Binding Bacteria |
| Asialo GM1 | Gal$\beta$1-3<u>GalNAc$\beta$1-4Gal</u>$\beta$1-4Glc$\beta$1-1Cer |
| Asialo GM2 | <u>GalNAc$\beta$1-4Gal</u>$\beta$1-4Glc$\beta$1-1Cer |
| Sulfatide | SO$_3^-$—Gal$\beta$1-1Cer |
| Galactosyl Ceramide (CMH) | Gal$\beta$1-1Cer |
| Lactosyl Ceramide (CDH) | Gal$\beta$1-4Glc$\beta$1-1Cer |
| Trihexosyl Ceramide (CTH) | Gal$\alpha$1-4Gal$\beta$1-4Glc$\beta$1-1Cer |
| Paragloboside | Gal$\beta$1-4GlcNAc$\beta$1-3Gal$\beta$1-4Glc$\beta$1-1Cer |
| Globoside | GalNAc$\beta$1-3Gal$\alpha$1-4Gal$\beta$1-4Glc$\beta$1-1Cer |
| Forssman | GalNAc$\alpha$1-3GalNAc$\beta$1-3Gal$\alpha$1-4Gal$\beta$1-4Glc$\beta$1-1Cer |
| GM1 | Gal$\beta$1-3GalNAc$\beta$1-4[NeuAc$\alpha$2-3]Gal$\beta$1-4Glc$\beta$1-1Cer |
| GM2 | GalNAc$\beta$1-4[NeuAc$\alpha$2-3]Gal$\beta$1-4Glc$\beta$1-1Cer |
| GM3 | NeuAc$\alpha$2-3Gal$\beta$1-4Glc$\beta$1-1Cer |
| GD1a | NeuAc$\alpha$2-3Gal$\beta$1-3GalNAc$\beta$1-4[NeuAc$\alpha$2-3]Gal$\beta$1-4Glc$\beta$1-1Cer |
| GD1b | Gal$\beta$1-3GalNAc$\beta$1-4[NeuAc$\alpha$2-8NeuAc$\alpha$2-3]Gal$\beta$1-4Glc$\beta$1-1Cer |

[a]The underline indicates the probable minimum sequence required for binding.

Further, no binding was detected to total glyolipids from about 50 mg net weight of human meconium, sheep erythrocytes, hog gastric mucosa, bovine trachea or human type O erythrocytes (data not shown). A binding pattern identical to that in FIG. 5B was also observed when the plate was incubated with labeled P. cepacia and the other four strains of P. aeruginosa tested. Interestingly, Pseudomonas did not bind to paraglobo-side, which contains terminal Galβ1-4GlcNAc, a carbohydrate sequence reported to inhibit binding of P. aeruginosa to mucus. Both P. aeruginosa and P. cepacia also failed to bind to GM1, GM2, GD1a, and GD1b suggesting that the sialosyl residues prevent binding. The finding that these bacteria did not bind to lactosylceramide also suggests that β-N-acetylgalactosamine, which is positioned internally in asialo GM1 and terminally is asialo GM2, is required. β-N-acetylgalactosamine itself, however, is not sufficient for binding as the bacteria did not bind to globoside, which contains a terminal GalNAcβ1-3Gal sequence, or to the Forssman glycolipid, which contains a terminal GalNAcα1-3Gal-NAc sequence as shown in FIG. 3.

Figure 6:
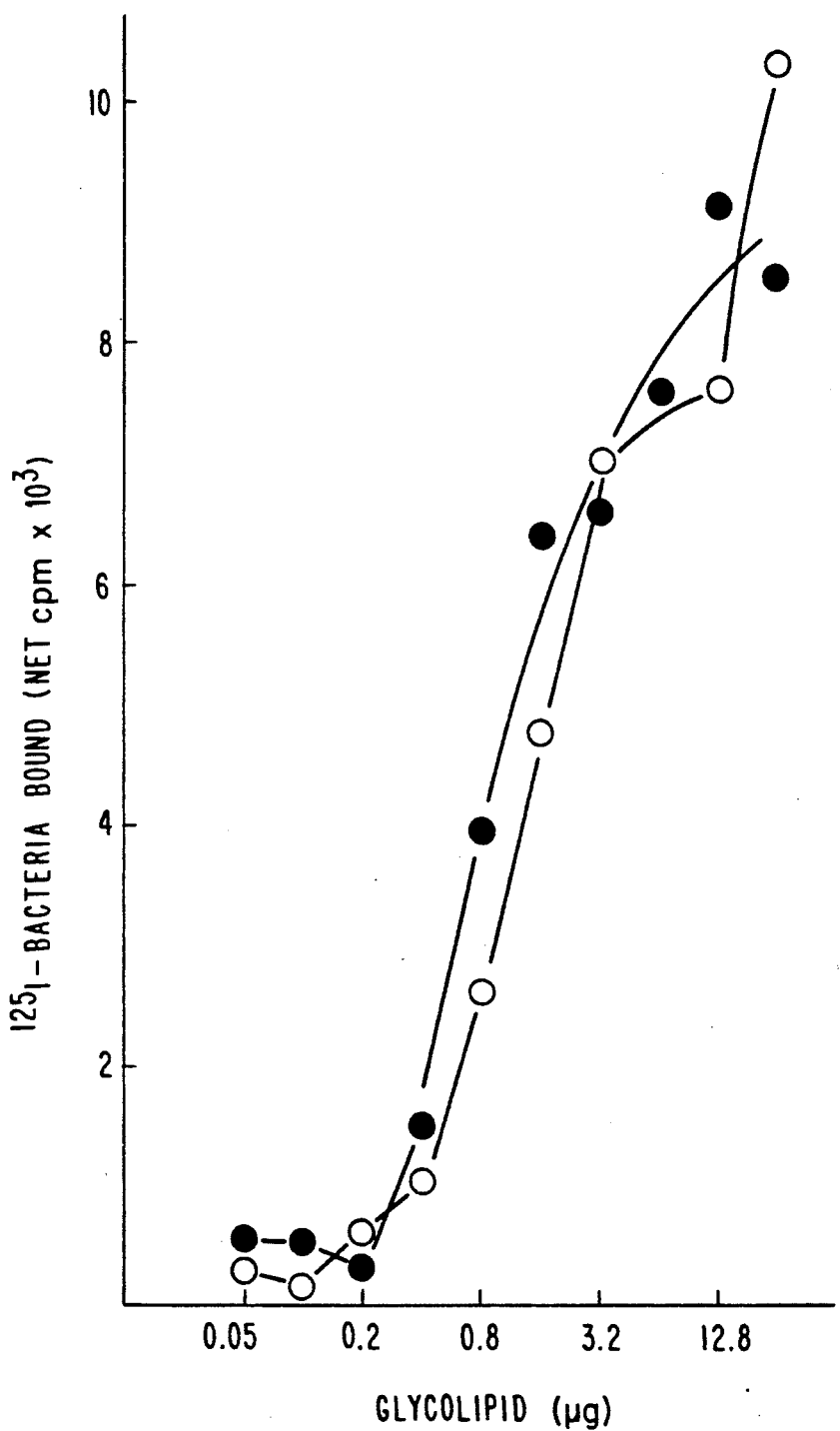
FIG. 6 illustrates the binding curve for $^{125}$I-labeled *P. aeruginosa* CT3 to receptor glycolipids serially diluted into polyvinylchloride microtiter wells.

To estimate the avidity of P. aeruginosa and P. cepacia for asialo GM1 and asialo GM2, glycolipids were serially diluted in 25 µl of methanol containing 100 ng each of the auxillary lipids phosphatidyl choline and cholesterol in flat bottom wells o polyvinylchloride microtiter plates (Falcon 3912-III, Becton-Dickerson). After the solutions were dried by evaporation, the wells were filled with TBS-BSA, emptied after 2 hours, and incubated with 25 µl of approximately $5 \times 10^6$ cells ($2 \times 10^5$ cpm). After 4 hours the wells were emptied, washed 5 times, with TBS-BSA, and cut from the plate, and bound radioactivity was quantified in a gamma counter. As shown in FIG. 6, both asialo GM1 and asialo GM2 exhibit similar binding curves in the solid phase binding assay indicating that both glycolipids bind the bacteria equally well. About 0.8 µg of glycolipids/well results in half-maximum binding of P. aeruginosa (and P. cepacia, data not shown). At 10 µg of glycolipid/well, lactosylceramide and GM1 did not bind the bacteria.

P. cepacia, which is now isolated with increasing frequency from patients with CF, and all five strains of P. aeruginosa tested in this study specifically recognize the same carbohydrate sequence in glycolipids. Data from Vishwanth and Ramphal suggest that the potential target site for adherence of P. aeruginosa is mucus. Recently, Ramphal et al., Proc. IX Internat. Symp. Glyconconj., G131 (1987), presented indirect evidence that the receptor is carbohydrate, since milk oligosaccharides containing a Galβ1-4GlcNAc sequence inhibited binding of P. aeruginosa to mucus. The results of this example suggest that glycoconjugates other than mucins may be receptors for Pseudomonas. Because mucoid and nonmucoid strains share the same binding specificity, both cell types probably possess a common mechanism for adhesion. Whether pili or other outer membrane components are involved in binding is not known. P. aeruginosa contains a cell surface lectin not in pili that binds to and agglutinates various erythrocytes. Interestingly, neuraminidase-treated erythrocytes are more easily agglutinated. P. aeruginosa also has two other hemagglutinating lectins found mainly inside the cells.

Gylcolipids are possibly adhesion receptors for other bacteria. For example, uropathogenic Escherichia coli bind to glycolipids containing a terminal or internal Gal/1-4Gal sequence, and do not bind to an internal GalNAcβ1-4Gas sequence. Propionibacterium granulosum bind to glycolipids containing a terminal or internal Galβ1-4Glc sequence, and Actinomyces naeslundii bind to glycolipids containing either a Galβ1-3GalNAc or a GalNAcβ1-3Gal sequence In summary, this example demonstrates that P. aeruginosa and P. cepacia bind specifically to asialo GM1 and asialo GM2. There bacteria probably recognize at least terminal or internal GalNAcβ1-4Gal sequences in the saccharide chain. Whether this binding specificity is related to the high susceptibility of CF patients to colonization by these bacteria remains to be seen.

The results of Example 2 are better understood from FIGS. 5 and 6.

FIG. 5 illustrates the direct binding of $^{125}$I-labeled P. aeruginosa CT3 to glyolipids separated by thin layer chromatography. The chromatography and thin-layer overlay procedure were carried out as described in the text. Panel A is a standard glycolipids detected with orcinol reagent. Panel B is a glycolipids detected by autoradiography with P. aeruginosa. Lane 1 is 2 µg galactosyl ceramide (CMH), 1 µg lactosyl ceramide (CDH), 1 µg trihexosyl ceramide (CTH), 1 µg globoside (GL4), and the gangliosides GM3 (1 µg), GM2 (0.5 µg), GM1 (1 µg), and GD1a (2 µg). Lane 2 is µg gangliotetraosylceramide (asialo GM1). Lane 3 is 2 µg ganglio-N-triaosylsylceramide (asialo GM2). Lane 4 is 1 µg paragloboside.

FIG. 6 illustrates the binding curve for $^{125}$I-labeled P. aeruginosa CT3 (approximately $10^7$ cells/well) to glycolipids serially diluted into polyvinylchloride microtiter wells. The solid phase binding assay was carried out as described in the test. A solid circle (●) is asialo GM1 and an empty circle (○) is asialo GM2.

The following abbreviations are used in Example 2: CF, cystic fibrosis; PBS, phosphate-buffered saline; TBS-BSA, 0.05M Tris buffered saline, pH 7.8, containing 1 percent bovine serum albumin and 0.1 percent sodium azide; Cer, Ceramide; CMH, Galβ1-1Cer; CDH, Galβ1-4Glcβ1-1Cer; CTH, Galα1-4Galβ1-4Glcβ1-1Cer; GL4, GalNAcβ1-3Galα1-4Galβ1-4Glcβ1-1Cer; GM1, Galβ1-3GalNAcβ1-4[NeuAc 2-3]-Galβ1-4Glcβ1-1Cer; GM2, GalNAcβ1-4[NeuAc 2-3]Galβ1-4Glcβ1-1Cer; GM3, NeuAc/2-3Galβ1-4Glcβ1-1Cer; GD1a, NeuAcα2-3Galβ1-3GalNAcβ1-4[NeuAcα2-3]-Galβ1-4Glcβ1-1Cer; asialo GM1, Galβ1-3GalNAcβ1-4Galβ1-4Glcβ1-1Cer; asialo GM2, GalNAcβ1-4Galβ1-4Glcβ1-1Cer.

What is claimed is:

1. A composition of matter which contains a carrier and a pathogenic bacteria bound to a purified receptor containing a carbohydrate moiety of the structure N-acetylgalactosamine-beta-1-4-galactose-beta-1-4-glucose.

2. A composition of claim 1 wherein the carrier is an insoluble carrier.

3. A composition of claim 2 wherein the carrier is a microtiter plate.

* * * * *